United States Patent [19]

Villacorta et al.

[11] Patent Number: 5,440,062
[45] Date of Patent: Aug. 8, 1995

[54] ENANTIOSELECTIVE ADDITION OF HYDROCARBONS TO ALPHA,BETA-UNSATURATED CARBONYL COMPOUNDS

[75] Inventors: Gilberto M. Villacorta, Hoboken, N.J.; Kwang-Hyun Ahn, Somerville; Stephen J. Lippard, Cambridge, both of Mass.

[73] Assignee: Massachusetts Institute of Technology, Boston, Mass.

[21] Appl. No.: 974,132

[22] Filed: Nov. 10, 1992

Related U.S. Application Data

[60] Division of Ser. No. 349,584, May 9, 1989, Pat. No. 5,162,586, which is a continuation-in-part of Ser. No. 193,246, May 11, 1988, Pat. No. 4,962,214.

[51] Int. Cl.$^6$ ............................................. C07F 1/08
[52] U.S. Cl. ....................................... 556/33; 556/28
[58] Field of Search ................................... 556/33, 28

[56] References Cited

U.S. PATENT DOCUMENTS

| | | | |
|---|---|---|---|
| 3,052,705 | 9/1962 | Brasen et al. | 260/439 |
| 3,177,232 | 4/1965 | Muetterties | 260/429.7 |
| 3,876,675 | 4/1975 | Trofimenko | 260/429 J |
| 4,471,130 | 9/1984 | Katsuki et al. | 549/523 |

OTHER PUBLICATIONS

Grant J., *Hackh's Chemical Dictionary*, Fourth Ed. McGraw–Hill Book Company. (1969) New York, p. 331.

Brunner, H. and Knott, A., "Asymmetric Catalyses XXVII*. Rh Complexes with Optically Active Ligands Derived from Tropolone," *J. of Organometallic Chemistry*, 295:211–221 (1985).

Posner, G. H. and Hulce, M., "Enantiocontrolled Synthesis of (S)-3-Substituted Cycloalkanones from (S)-2-(p-Tolylsulfinyl)-2-Cycloalkenones and Diorganomagnesium Reagents," *Tetrahedron Letters*, 25(4):379–382 (1984).

Villacorta, G. M. and Lippard, S. J., "Tropocoronands: A Versatile Macrocyclic Ligand System for Mononuclear and Binuclear Metal Complexes," *Pure & Appl. Chem.*, 58(11):1477–1484 (1986).

Villacorta, G. M., et al., "Dicopper(I) Tropocoronands: Synthesis, X-ray Crystal Structure, and Spectral properties of Neutral Binuclear Copper(I) Complexes Bridged by Symmetrically Substituted Alkynes," *J. Am. Chem. Soc.*, 107:6732–6734 (1985).

Dieter, R. K. and Tokles, M., "Asymmetric Induction in the Conjugate Addition Reactions of Chiral Organo(hetero)cuprates," *J. Am. Chem. Soc.*, 109:2040–2046 (1987).

Lipshutz, B. H., et al., "The Chemistry of Higher Order Organocuprates," *Tetrahedron*, 40(24):5005–5038 (1984).

Lipshutz, B. H., et al., "Substitution Reactions of Secondary Halides and Epoxides with Higher Order, Mixed Organocuprates, $R_2Cu(CN)Li_2$: Synthetic, Stereochemical, and Mechanistic Aspects," *J. Org. Chem.*, 49:3928–3938 (1984).

Corey, E. J., et al., "Enantioselective Conjugate Addition of Rationally Designed Chiral Cuprate Reagents to 2-Cycloalkenones," *J. Am. Chem. Soc.*, 108:7114–7116 (1986).

Davis, W. M. and Lippard, S. J., "Tropocoronands as Binucleating Ligands. Synthesis, Structure and Properties of a ($\mu$-Acetato)($\mu$-methoxo)dicopper(II) Derivative," *Inorg. Chem.*, 24:3688–3691 (1985).

Villacorta, G. M., et al., "Alkyne–Bridged Dicopper(I) Complexes of the Tropocoronand Macrocycles," *Organometallics*, 6:2426–2431 (1987).

(List continued on next page.)

*Primary Examiner*—Peter O'Sullivan
*Attorney, Agent, or Firm*—Hamilton, Brook, Smith & Reynolds

[57] ABSTRACT

The conjugate addition of hydrocarbon equivalents to alpha,beta-unsaturated carbonyl compounds using a series of novel catalysts is described. The catalysts comprise copper(I) complexes with ligand systems comprising either tropocoronand macrocycles or N,N'-dialkyl-substituted aminotroponeimines.

5 Claims, No Drawings

OTHER PUBLICATIONS

Villacorta, G. M. and Lippard, S. J., "Dicopper(I) Carbonyl Tropocoronands. Preparation, Structural Characteristics and Reactivity of Neutral Binuclear Cu-CO Macrocyclic Compounds," *Inorg. Chem.*, 26:3672–3676 (1987).

Villacorta, G. M. and Lippard, S. J., "Synthesis, Structure Determination and Stereoisomerism of Dirhodium(I) Tetracarbonyl Tropocoronand Complexes," *Inorg. Chem.*, 27:144–149 (1988).

Villacorta, G. M., et al., "Synthesis and Reactivity of Binuclear Tropocoronand and Related Organocopper(I) Complexes, Catalytic Enantioselective Conjugate Addition of Grignard Reagents to 2-Cyclohexen-1-one," *J. Am. Chem. Soc.*, 110:3175–3182 (1988).

Fryzuk, M. D. and Bosnich, B., "Asymmetric Synthesis. An Asymmetric Homogeneous Hydrogenation Catalyst Which Breeds Its Own Chirality," *J. Am. Chem. Soc.*, 100:5491–5494 (1978).

Eaton, D. R., et al., "Synthesis and Magnetic Resonance Studies of Some Paramagnetic Transition Metal Aminotroponiminates," *Inorg. Chem.*, 7(10):2040–2046 (1968). (From Chem. Abstracts, 1968, 69, Abstract No. 22).

Bertz, S. H., et al., "Asymmetric Induction with Amidocuprates," *J. Org. Chem.*, 51:4953–4959 (1986).

ENANTIOSELECTIVE ADDITION OF HYDROCARBONS TO ALPHA,BETA-UNSATURATED CARBONYL COMPOUNDS

GOVERNMENT SUPPORT

Work described herein was supported by Grant No. NSF CHE 85-42205 from the National Science Foundation.

This application is a division of application Ser. No. 07/349,584 filed on May 9, 1989, issued as U.S. Pat. No. 5,162,586 on Nov. 10, 1992 which is a Continuation-in-Part application of Ser. No. 07/193,246, filed May 11, 1988, issued as U.S. Pat. No. 4,962,214, on Nov. 9, 1990.

BACKGROUND OF THE INVENTION

Many enantiomerically pure cycloalkanones substituted at the 3-position with hydrocarbon groups are useful as both synthetic intermediates and as physiologically active natural products. For example, the plant stress metabolite solavetivone methylenomycin is an (R)-3-methylcyclohexanone and the anti-tumor eudesmanolide pinnatifidin is an (S)-3-methylcyclohexanone. Posner et al., *Tetrahedron Lett.*, 25(4), 379 (1984). Traditionally, these compounds have been formed by the stoichiometric addition of hydrocarbon groups to cycloalkanones.

Another application of the stoichiometric addition of hydrocarbon groups to cycloalkanones has been in the production of prostaglandins. The prostaglandin family is known to control a wide variety of physiological responses in human and animal tissues. In particular, the prostaglandins are known to be involved in the regulation of systems including the circulatory system, the respiratory system and the digestive system.

Prostaglandins derived from synthetic processes have been employed in a variety of pharmaceuticals. For example, the prostaglandin 15-deoxy-16-hydroxy-16-methyl-PGE methyl ester has been shown to be a potent anti-ulcer drug. The formula for this particular prostaglandin is as follows:

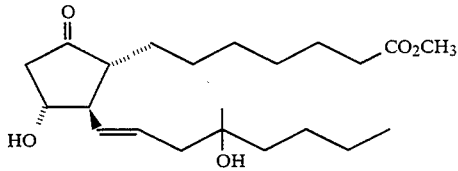

In the synthesis of prostaglandins, a stoichiometric conjugate addition reaction of an organocopper reagent to cyclopentenone has been employed as a key step. This addition proceeds as follows:

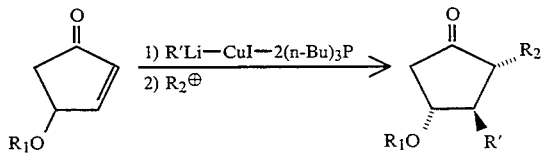

The stoichiometric synthesis of prostaglandins is more fully described by R. Noyori et al., in *Angew. Chem. Int. Ed. Engl.* 23, 847–876 (1984).

Stoichiometric reactions of the type described above may produce products having high enantiomeric excesses; however, they still require one equivalent of reagent per one equivalent of optically active product. Previous workers have attempted to develop catalytic enantioselective systems for other types of reactions with mixed results. Most notably, catalytic asymmetric hydrogenation of unsaturated compounds has been demonstrated by Bosnich and co-workers using rhodium-phosphine catalysts (Fryduk, M. P. and Bosnich, B., *J. Amer. Chem. Soc.* 100:5491 (1978). Sharpless and co-workers have discovered the asymmetric epoxidation of allylic alcohols by alkyl hydroperoxides with excellent enantiomeric excess (e.e.) utilizing titanium-tartrate catalysts. (Katsuki, T. and Sharpless, K. B., U.S. Pat. No. 4,471,130.) Brunner et al. have attempted a catalytic enantioselective hydrosilylation of acetophenone using a rhodium complex of N,N-di(s,s,-phenethyl) aminotroponeimino with poor results (Brunner, H. et al., *T. Organomet. Chem.* 295:211–221 (1985)).

A reagent system which successfully provides for the catalytic production of optically active $\beta$-substituted alkanones would be of great utility. Thus, a need exists for reagents and methods which catalytically enhance the production of beta-substituted cycloalkanones of high enantiomeric purity.

SUMMARY OF THE INVENTION

This invention pertains to optically active compounds which serve as auxiliary ligands for the production of novel organometallic reagents. This invention further pertains to the use of these organometallic reagents as catalysts which promote the enantioselective addition of hydrocarbon groups to cycloalkenones. More specifically, the invention pertains to the conjugate addition of Grignard reagents, RMgCl (where R—Ph, n—Bu, Me and other organic groups), to cyclohexenones using catalysts which comprise complexes of copper(I) compounds.

In one catalyst described herein, copper(I) alkyls are complexed with chiral ligands based on N,N'-dialkyl-substituted aminotroponeimines. When these catalysts are employed in the addition of hydrocarbon equivalents to cycloalkenones, optically active compounds are produced.

Thus, in one embodiment of the invention, asymmetric induction in a highly regiospecific catalytic conjugate addition of Grignard reagents to cyclohexenone is accomplished. With the addition of chelating and silyl reagents to the reaction mixture, this reaction can be made highly enantioselective, producing in some cases products having an enantiomeric excess of approximately 80%.

In another catalyst described herein, alkyl-bridged dicopper(I) compounds are complexed with tropocoronand macrocycles. These catalysts are useful for the production of racemic 3-substituted cyclohexanones. Additionally, other copper(I) chelates are useful, as described in the following section.

DETAILED DESCRIPTION OF THE INVENTION

Individual aminotroponeimine groups containing metallic species are found to be useful in the formation of optically active organometallic reagents which can be effectively used to catalyze a variety of asymmetric syntheses, including the conjugate addition of chiral organocuprate reagents to cyclohexenones. A wide variety of useful chemical species can thus be produced using this catalytic process to provide products useful as, for example, pharmaceuticals. Both chiral and achiral reagents for the catalytic addition of hydrocarbon equivalents to unsaturated carbonyl compounds are described herein. Additionally, methods for producing and using these reagents are described.

Additionally, the versatility of tropocoronand macrocycles, H₂(TC-n,n'), as binucleating ligands has recently been demonstrated. See, for example, Villacorta et al., *Pure and Appl. Chem.*, 58, 1477 (1986); Villacorta et al., *J. Am. Chem. Soc.*, 107 6732 (1985); Davis et al., *Inorg. Chem.*, 24, 3688 (1985); Villacorta et al., *Organometallics*, 6, 2426 (1987); Villacorta et al., *Inorg.. Chem.*, 26, 3672 (1987) and Villacorta et al., *Inorg. Chem.*, 27, 144 (1988). The tropocoronands are derived from aminotroponeimines, a class of chelating bidentate nitrogen donor ligands long studied in transition metal coordination chemistry. The tropocoronand complex has the following structure:

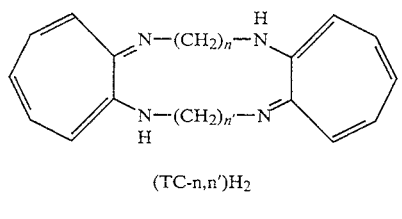

(TC-n,n')H₂ n,n' = 3,3;4,4;4,5;5,5;6,6

Tropocoronands are constructed by linking two aminotroponeimine groups with polymethylene chains to form macrocyclic rings of variable size. These molecules bind low oxidation state late transition metals such as Cu(I) and Rh(I). Complexes previously characterized include alkyne-bridged dicopper(I), dicopper(I), dicarbonyl and dirhodium(I) tetracarbonyl derivatives. Although these complexes exhibit structural features such as syn-anti-diastereoisomerism, very little synthetic utility is found for them.

Stoichiometry of the Conjugate Addition

It is first useful to present stoichiometric details of the known, non-catalytic, conjugate addition reaction utilizing tropocoronands. When a yellow tetrahydrofuran (THF) solution of Li₂(TC-5,5)(0.5 equiv) and a yellow suspension of (CuR)ₙ in THF are combined at −78° C. and allowed to warm up gradually, an air-sensitive burgundy solution of a tropocoronand dicopper(I) alkyl complex (TDAC) forms (eq. 1).

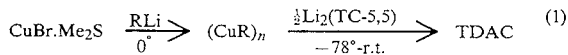

The homogeneous solution of the TDAC, when treated with cyclohexenone (1.0 equiv per Cu), produces no conjugate addition products. Only unreacted cyclohexenone and small amounts of products resulting from coupling of R fragments (e.g., biphenyl or octane) for R—Ph or Bu, respectively, are detected (eq. 2).

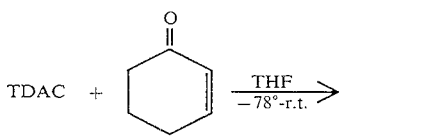

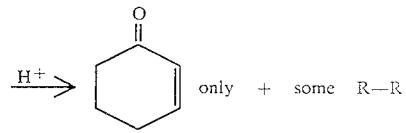

When the TDAC is pretreated at −78° C. with RLi (1.0 equiv per Cu), a reaction accompanied by a slight darkening of the burgundy solution, and then allowed to react with cyclohexenone (1.0 equiv) at −78° C., 3-alkylcyclohexanone product is produced immediately after quenching of the reaction mixture (eq. 3).

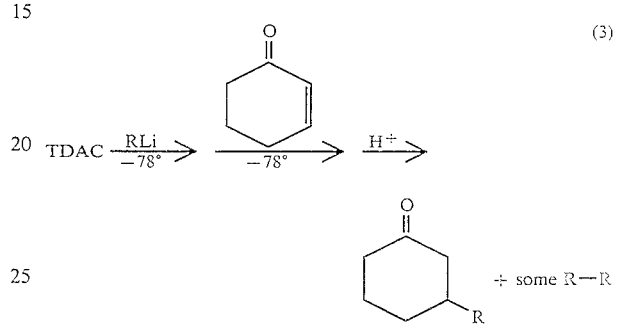

The intensity of the burgundy color returns to its original shade after addition of the cycloalkenone, and no solids are observed over the course of the fast reaction. A small amount of coupled product, R—R, is still present. The persistence of the deep burgundy color and the absence of any precipitate are taken as evidence that a TDAC is present throughout the course of the reaction and is responsible for the observed conjugate addition product in the presence of added alkyllithium or Grignard reagent.

Solutions of the Mononuclear Copper(II) complex, [Cu(TC-5,5)], yield only 1,2-addition products under conditions that produce only 1,4-addition with the TDAC (eq. 4).

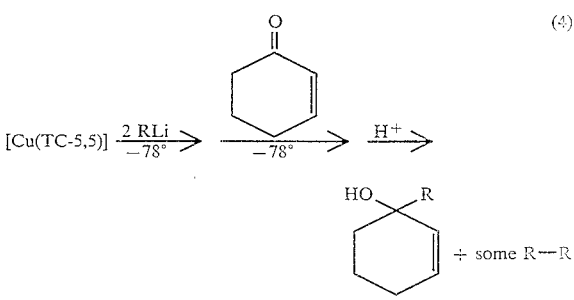

The RLi-pretreated TDAC's, with R—Ph, Bu and Me, undergo the "stoichiometric" reaction with cyclohexenone smoothly except that significant amounts (up to 20%) of the 1,2-addition product are obtained with R—Me.

Synthesis of Chiral Ligands

To assess the significance of optically active organometallic aminotroponeimine reagents as catalysts for the conjugate addition of hydrocarbon equivalents to alpha,beta-unsaturated carbonyl compounds, it is necessary to synthesize chiral N,N'-disubstituted aminotroponeimines. Although the chelating and metal-binding abilities of achiral analogs of these compounds are known, the achiral aminotroponeimines have been utilized primarily for the synthesis of mononuclear bis-(aminotroponeiminato) complexes of divalent first-row transition metals. The chiral ligands may be generally useful in forming 3-coordinate copper alkyl complexes. The aminotroponeimines (AMT's) may also stabilize organocopper compounds where other nitrogen donor ligands have failed. Other ligand systems employing imine-type donor functionalities, such as the diazabutadiene (DAB) or diazadiene and a number of imine-enamine (ImEn) derivatives, of the general formulae below, have been used in the synthesis of low-oxidation state metal alkyl and carbonyl compounds.

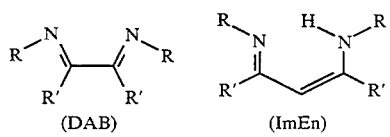

(DAB)            (ImEn)

Unlike these other ligand systems, however, the aminotroponeimines possess a highly localized electron distribution and are more resistant to attack by nucleophiles or electrophiles that may be present or added to the reaction medium. Not only can the AMT ligands be expected to maintain their chemical integrity in reaction media, but the wide variety of chiral amine carbon fragments that may be incorporated in the AMT adds to their potential synthetic utility as auxiliary ligands.

In one embodiment of the invention, a compound represented by the following resonance structure can be synthesized:

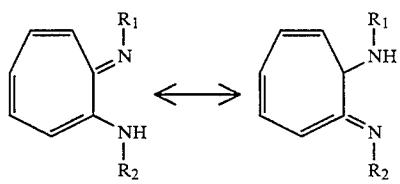

in which $R_1$ and $R_2$ may be the same or different and represent chiral hydrocarbon groups having 4 to 40 carbon atoms. In particular, a compound of the formula:

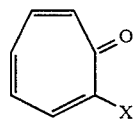

wherein X is a leaving group selected from the group consisting of halides, tosylates, triflates, mesylates and brosylates, is reacted with a primary amine of the formula $R_1$—$NH_2$ in a suitable solvent to produce an optically active compound having the formula:

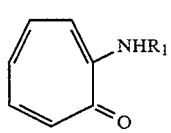

in which $R_1$ is a chiral hydrocarbon group having 4 to 40 carbon atoms. This compound is then reacted with a reagent selected from the group consisting of dimethyl sulfate and diethylsulfate, in a suitable aromatic solvent to produce a compound of the formula:

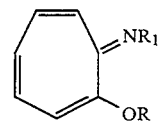

in which R is a methyl or an ethyl group and $R_1$ is described above. This compound is then reacted with a primary amine of the formula $R_2$—$NH_2$ in a suitable solvent and wherein $R_2$ is a chiral hydrocarbon group having 4 to 40 carbon atoms. Alternatively, in the final reaction step, R, is a hydrogen.

Scheme A outlines the three-step sequence employed to synthesize the first chiral derivative, designated herein as H(CHIRAMT). The process readily leads to the production of multigram quantities of pure H(CHIRAMT).

Scheme A

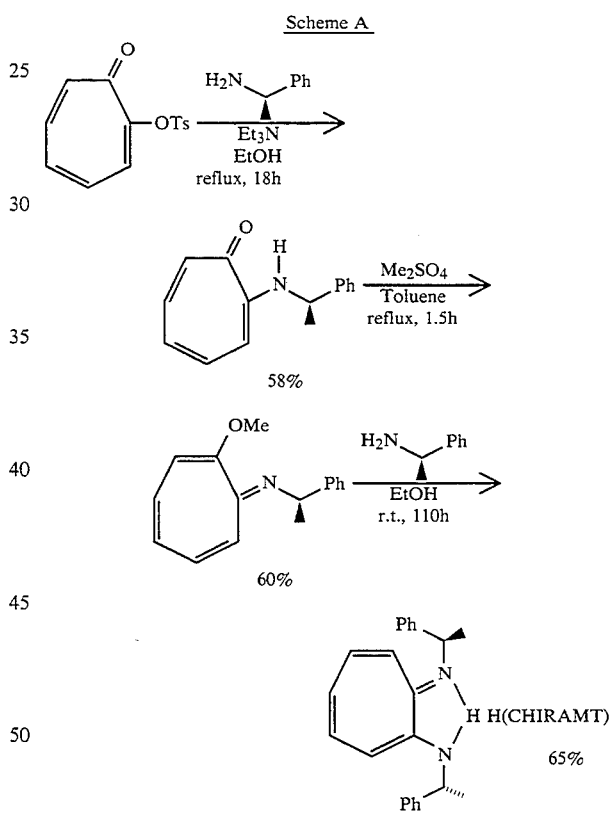

Asymmetric Induction Catalyzed by Chiral Cuprate Complexes

A yellow mixture of $(CuR)_n$ and Li(CHIRAMT) at $-78°$ C. in THF forms a homogenous burgundy solution upon warming (eq. 5).

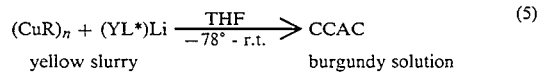

$$(CuR)_n + (YL^*)Li \xrightarrow[-78° \text{ - r.t.}]{THF} CCAC \qquad (5)$$

yellow slurry           burgundy solution

The species in solution, referred to as the chiral copper alkyl complex (CCAC), is unreactive towards added cyclohexenone. Pretreatment with RLi (1.0 equiv. per Cu), followed by addition of the cycloalkenone at $-78°$ C., leads to the instantaneous and regiospecific production of the Michael-like adduct, however (eq. 6).

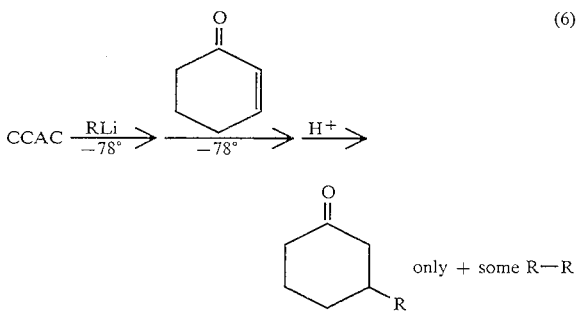

Once again, a small amount of R—R coupled product is detected, but the the reaction produces little, if any, 1,2-addition product. Thus, fresh solutions of the CCAC are efficient catalysts for the conjugate addition of Grignard reagents (R—Ph, Bu) to cyclohexenone. Even a complex formed from $CuBr.Me_2S$ and Li(-CHIRAMT) provides useful amounts of product.

The chemistry of the CCAC yields 3-alkylcyclohexanone products which are optically active. An enantiomeric purity of as high as approximately 80% is observed in the presence of hexamethylphosphoric triamide (HMPA) and a silyl reagent. These values are significant because they were achieved in a system where the chiral ligand-to-substrate ratio is 0.04. This ratio is approximately 200 times less than that described in recently published work in which values of 88% ee were observed for the stoichiometric addition. Dieter et al., *J. Am. Chem. Soc.*, 109, 2040 (1987). These results illustrate the utility of chiral AMT-based catalysts in organic synthesis.

It should be noted that, owing to the catalytic nature of the reaction, the R group in the final product is determined solely by the identity of the Grignard reagent. The sluggishness of methyl group transfer may make that species the ideal general catalyst where Me is retained. This conclusion is similar to that reached previously following studies of mixed-heteroorganocuprate chemistry. Lipshutz et al., *Tetrahedron*, 40, 5005 (1984); Lipshutz et al., *J. Org. Chem.*, 49, 3928 (1984).

A wide variety of H(CHIRAMT) complexes are useful in the present invention. As such, the invention pertains to N,N'-disubstituted aminotroponeimines of the formula:

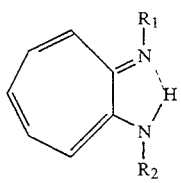

wherein $R_1$ and $R_2$ each represent chiral hydrocarbon groups, generally having 4 to 24 carbon atoms comprising aliphatic, aromatic, cyclic, or alicyclic groups or mixtures thereof, additionally with or without heteroatom substituents. For example, $R_1$ and $R_2$ can represent alkyl groups or amines used to synthesize the substituted aminotroponeimines, taken from but not limited to: (R)- or (S)-1-phenylethyl, (R)- or (S)-1-(1'-naphthyl) ethyl, (R)- or (S)-1-(9'-anthracenyl) ethyl, D-(−)-alanine, L-(+)-alanine, (R)- or (S)-2-amino-3-phenyl-1-propanol, (R)-(−)-1-amino-2-propanol, (S)-(+)-1-amino-2-propanol, (R)- or (S)-2-amino-1-propanol, (R)- or L-amphetamine, (R)- or (S)-norbornylamine, (R)- or (S)-fenchylamine, (R)- or (S)-bornylamine, 1-(R)-2-(S)-norephedrine and 1-(S)-2-(R)-norephedrine. Additionally, $R_1$ and $R_2$ may be the same, but are not necessarily so limited.

The H(CHIRAMT) complexes may then be used to form optically active organometallic reagents of the formula:

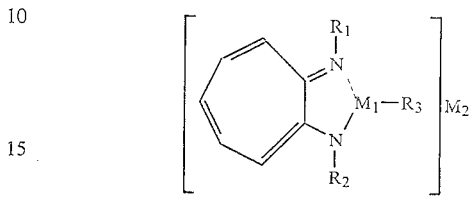

wherein $R_1$ and $R_2$ are as described above, $R_3$ represents a negatively charged group, such as a halogen or a hydrocarbon group of 1-24 carbon atoms, $M_1$ represents a transition metal atom and $M_2$ represents a positively charged counterion. In a preferred embodiment, $M_1$ is copper.

Although the optically active organometallic reagent is depicted as having the formula as shown above, it can also be described in terms of its components. The reagent is a solution comprising an optically active N,N'-disubstituted aminotroponeimine chelating ligand, a transition metal salt and an organometallic reagent (i.e., organomagnesium halide or organolithium reagent). The transition metal salt is $M_1X$ where $M_1$ is described below. The resulting optically active organometallic reagent can then be reacted with a slight excess of alpha,beta-unsaturated carbonyl compound and an additional amount of organomagnesium halide or organolithium reagent in slight excess of the alpha,beta carbonyl compound to produce an optically active beta-substituted carbonyl compound.

In the preferred embodiments, the N,N'-disubstituted aminotroponeimine comprises 1-[(R)-α-methylbenzylamino]-7-[(R)-α-methylbenzylamino]-1,3,5-cycloheptatriene, 1-[(S)-α-methylbenzylamino]-7-[(S)-α-methylbenzylamino]-1,3,5-cycloheptatriene, 1-[(R)-1-(1'-napthyl)ethylamino]-7-[(R)-1-(1'-naphthyl)ethylimino]-1,3,5-cycloheptatriene, 1-[(S)-1-(1'-naphthyl)ethylamino]-7-[(S)-1-(1'-naphthyl)ethylimino]-1,3,5-cycloheptatriene, 1-[(R)-1-(9'-anthracenyl)ethylamino]-7-[(R)-1-(9'-anthracenyl)ethylimino]-1,3,5-cycloheptatriene, and 1-[(S)-1-(9'-anthracenyl)ethylamino]-7-[(S)-1-(9'-anthracenyl)ethylimino]-1,3,5-cycloheptatriene.

Using the steps outlined herein, other aminotroponeimines can be used to form the organometallic reagents as well. These other aminotroponeimines can be produced using chiral groups which include, but are not limited to: (R)- or (S)-1-phenylethyl, (R)- or (S)-1-(1'-naphthyl) ethyl, (R)- or (S)-1-(9'-anthracenyl) ethyl, D-(−)-alanine, L-(+)-alanine, (R)- or (S)-2-amino-3-phenyl-1-propanol, (R)-(−)-1-amino-2-propanol, (S)-(+)-1-amino-2-propanol, (R)- or (S)-2-amino-1-propanol, (R)- or L-amphetamine, (R)- or (S)-norbornylamine, (R)- or (S)-fenchylamine, (R)- or (S)-bornylamine, 1-(R)-2-(S)-norephedrine and 1-(S)-2-(R)-norephedrine. Additionally, $R_1$ and $R_2$ may be the same, but are not necessarily so limited.

Preferably, $M_1$ is selected from the group consisting of copper, silver, gold, nickel, palladium, platinum, cobalt, rhodium, iridium, iron, ruthenium, osmium, molybdenum, tungsten, titanium, vanadium and zinc.

M₂ is preferably selected from the group consisting of alkali metals, alkaline-earth metals, quaternary amines, quaternary arsines and quaternary phosphines.

In the preferred embodiment, an optically active beta-substituted carbonyl compound can be produced by means of a catalytic enantioselective addition of hydrocarbon to alpha,beta-unsaturated carbonyl compounds. The method comprises providing an optically active organometallic reagent; a solution of an alpha,-beta-unsaturated carbonyl compound in a suitable solvent, preferably in slight excess of the amount of N,N'-disubstituted aminotroponeimine; and an organometallic reagent (i.e., an organomagnesium halide or organolithium reagent) solution of a desired hydrocarbon, preferably in slight excess of the amount of N,N'-disubstituted aminotroponeimine. The three are mixed together simultaneously and at about the same rate. The resulting reaction mixture is stirred for a time sufficient to allow the reaction to proceed substantially to completion, thereby forming products. The reaction mixture is quenched with a protic solution and the optically active beta-substituted carbonyl compound is isolated.

In another embodiment, an additive, such as TMEDA, HMPA, or various silyl compounds described below, can be added to the optically active organometallic reagent prior to the enantioselective addition reaction.

The mechanism for the enantioselective addition is currently believed to be as follows:

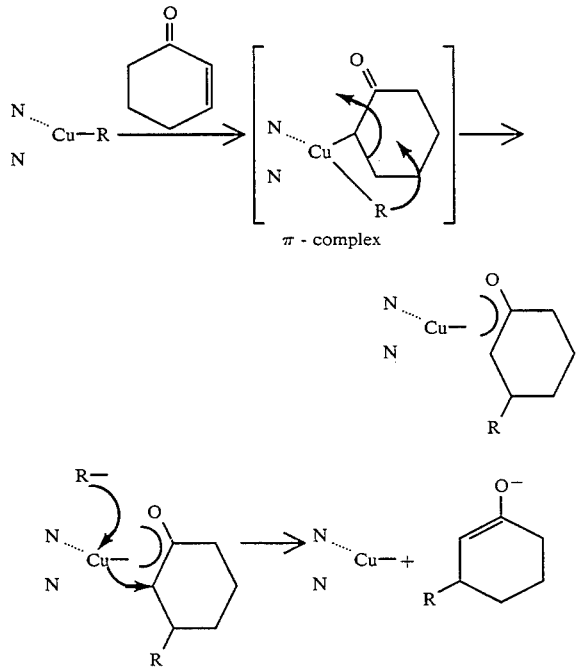

The copper centers are believed to accommodate the π-donor (enone), forming an intermediate 18e⁻ π-complex from which Michael-like adducts may emerge. This proposed mechanism does not invoke the commonly assumed intermediacy of copper(III) beta-adducts.

Additionally, a variety of additives can be used to facilitate this reaction and, perhaps, add bulk to the overall reagent complex. These additives include silyl compounds such as Me₃SiCl, phenyl₂(t—Bu)SiCl, (t—Bu)₂MeSiTfl and (i—Pr)₃SiTfl in combination with solvents such as toluene, N,N,N',N'-tetramethylenediamine (TMEDA), and hexamethylphosphoric triamide (HMPA). In the silyl compounds, the notation Tfl refers to trtfluoromethanesulfonate.

Synthesis of Achiral Reagents

Tropocoronand-derived reagents can be used to produce catalytically racemic product mixtures. These achiral reagents are similar in some aspects to the chiral aminotroponeimine reagents previously described.

Addition of 12-crown-4 to reaction mixtures produced by complexation of two equivalents of either CuBr or CuR with the dilithium salt of (TC-5,5) allows the isolation of dinuclear anionic tropocoronand complexes with well-separated copper cations. The copper(I) atoms are in a trigonal-planar geometry. This 3-coordinate configuration of the copper atoms is characteristic of all di-copper(I) tropocoronand complexes structurally examined to date. These compounds include neutral alkyne-bridged arrangements, as well as carbon monoxide adducts in which the (Cu—CO) moieties are located on opposite faces of the macrocycle. The trigonal-planar geometry appears to be preferred by dicopper(I) tropocoronand complexes, whether neutral or charged.

Using this pattern of coordination and the well-recognized ability of aryl groups to bridge metal ions, compounds such as [Li(12-crown-4)₂] [Cu₂(μ-Ph)(TC-5,5)], can be produced. It appears that a species formulated as Li[Cu₂(μ-R)(TC-5,5)] (the TDAC) forms directly at the elevated temperatures (i.e., greater than −30° C.) needed for complexation, characterized by a yellow-to-burgundy color change, to take place. The alkyl-bridged di-copper(I) core may be sufficiently stable to account for its inertness towards cyclohexenone. In the presence of excess nucleophilic reagent at −78° C., however, a new species forms, which contains perhaps two trigonal-planar copper(I) atoms bearing terminal alkyl groups. It reacts readily with the enone. Scheme B below outlines a proposed catalytic mechanism.

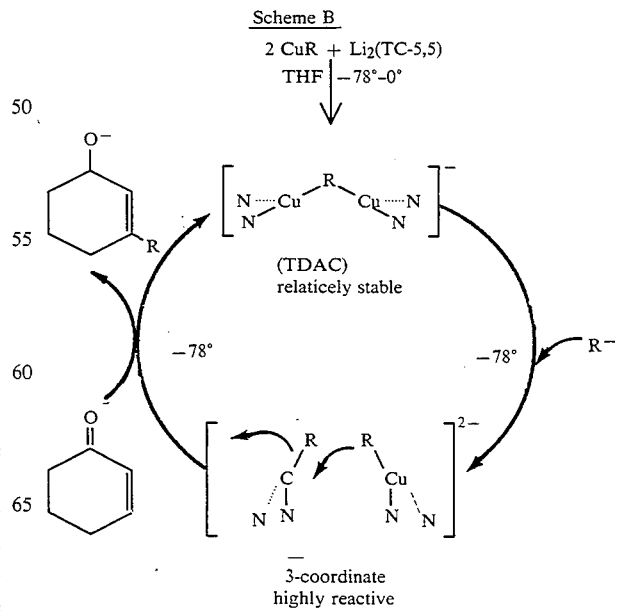

Thus, as can be seen in Scheme B, once the bridging mode of the TDAC is broken by excess nucleophile, the mechanism of the catalytic addition reaction is believed to be the same as for the individual H(CHIRAMT) reagents.

The reaction of $Li_2(TC-5,5)$ with 2.0 equiv of $CuBr\cdot Me_2S$ and excess 12-crown-4 produces a compound of limited solubility consistent with its ionic nature (eq. 7).

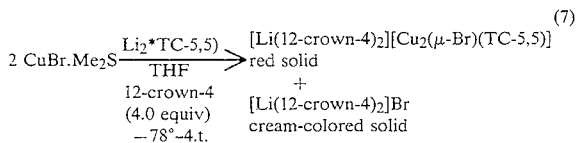

This binuclear compound (compound 1), which represents an anionic complex of the tropocoronand macrocycles, is air- and temperature-sensitive. Red solutions of the compound in THF, in which it is only sparingly soluble, quickly turn dark brown upon exposure to oxygen or upon standing for extended periods at room temperature, even in sealed tubes. The compound is stabilized by the crown ether, a class of molecule previously employed to stabilize sensitive species. Without 12-crown-4, the chemistry proceeds as indicated by eq. 8, in which the principal products are metallic copper and the known mononuclear cupric complex, $[Cu(TC-5,5)]$.

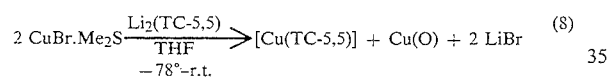

This disproportionation reaction has been previously observed for binuclear copper(I) tropocoronands.

Compound 1 is also produced indirectly and is present as a contaminant in product mixtures obtained from the chemistry shown in equation 9.

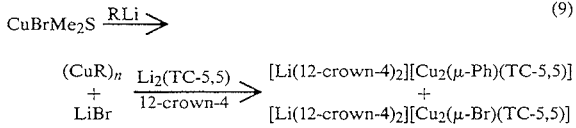

It is possible that $[Li(12\text{-}crown\text{-}4)_2][Cu_2(\mu\text{-}R)\text{-}(TC\text{-}5,5)]$, the main synthetic target of the above equation, undergoes a substitution reaction involving bromide ion to produce significant quantities of $[Li(12\text{-}crown\text{-}4)_2][Cu_2(\mu\text{-}Br)(TC\text{-}5,5)]$. While the crown ether molecule stabilizes complexes such as compounds produced by equation 9 by coordinating the lithium ion, this reaction also affords free bromide ion which can compete successfully for available copper(I) centers.

These results indicate that, in order to isolate pure samples of complexes such as $[Li(12\text{-}crown\text{-}4)_2][Cu_2(\mu\text{-}Ph)(TC\text{-}5,5)]$, halide free solutions are necessary. Tetrakis(acetonitrile)copper(I) having a non-coordinating counter ion is therefore employed. Although commonly used as a copper(I) source in inorganic chemistry, $[Cu(NCCH_3)_4](BF_4)$, has not been used as commonly as the cuprous halides in the preparation of copper-based reagents in organic synthesis. Possibly, side reactions involving the RLi or RMgCl reagents and the $CH_3CN$ groups of the copper(I) precursor were a concern. As demonstrated by the successful synthesis of the phenyl-bridged dicopper(I) tropocoronand, however, the metal atom is apparently more reactive towards phenyllithium, at least, than are the coordinated acetonitrile groups (equation 10).

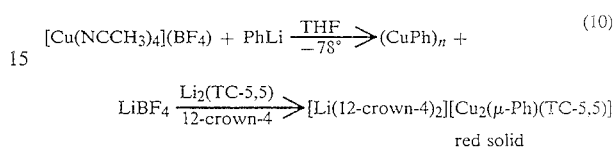

This fact, together with the ease of preparation and storage of $[Cu(NCCH_3)_4](BF_4)$, may make it a viable alternative to the cuprous halides where the absence of potentially coordinating ligands is desired.

Catalytic Activity. Table I summarizes the product distribution and other features of the conjugate addition of Grignard reagents to cyclohexenone catalyzed by aminotroponeiminate copper(I) alkyl and bromide complexes.

TABLE I

Product Distribution of the Conjugate Addition of Grignard Reagents to Cyclohexenone Using Various Catalysts

| Catalyst | R | cat/enone, mole fract. | regio-selectivity 1,4/1,2 | Yield % | % ee |
|---|---|---|---|---|---|
| Li[Cu₂R(TC-5,5)] | Ph | 0.02 | 97 | 85 | |
| Li[Cu₂R(TC-5,5)] | Bu | 0.02 | >100 | 79 | |
| Li[Cu₂R(TC-5,5)] | Me | 0.02 | 4 | | |
| Li[12-crown-4)₂][Cu₂(μ-Br)(TC-5,5)] | Bu | 0.006 | 4 | 51 | |
| Li[12-crown-4)₂][Cu₂(μ-Ph)(TC-5,5)] | Bu | 0.02 | 6 | 62 | |
| Li[CuR(CHIRAMT)] | Ph | 0.04 | >100 | 93 | 4(S) |
| Li[CuR(CHIRAMT)] | Bu | 0.04 | >100 | 94 | 14(S) |
| Li[CuR(CHIRAMT)] | Me | 0.04 | 4 | 28 | |
| Li[CuBr(CHIRAMT)] | Bu | 0.02 | 19 | 73 | 15(S) |
| Li[CuR(NEAT)] | Bu | 0.04 | | 89 | 15 |

The reactions were carried out by adding equimolar THF solutions of RMgCl and cyclohexenone to a −78° C. THF solution of the catalyst. The regioselectivity was estimated from the relative integrated areas of glc peaks corresponding to these products (the dehydration of the tertiary alcohol during analysis was assumed). The yield was the combined yield after chromatography. The enantiomeric excess was determined by the ratio of diastereometric ketals as described in the experimental section (see below). The yield for Li[Cu₂Me(TC-5,5)] and the enantiomeric excess for Li[CuMe(CHIRAMT)] were not determined.

Of the catalysts listed, the ones prepared in situ by far perform the best with respect both to regiospecificity (about 100:1 favoring 1,4-addition) and chemical yield (greater than 85% isolated yield). These findings, excluding the poor performance in the case of R—Me, compare favorably with the results of recent work by others who concluded that conjugate addition reactions of organocopper reagents, whether stoichiometric or catalytic, are generally inefficient, slow, and much in need of improvement.

Table I also demonstrates that TDAC compounds are active as catalysts for the conjugate addition reaction. Displacement of bridging halide ion by excess alkyllithium reagent was recently demonstrated to occur in a Ti—Rh heterobimetallic complex. The use of less nucleophilic Grignard reagents in our case, however, may result in incomplete conversion of the μ-bromo complex to the copper(I) alkylating agent under the conditions of the experiment. Under such circumstances, accumulation of unconverted Grignard reagents would produce significant amounts of the product expected from its direct reaction with cyclohexenone, the 1,2-adduct, as subsequently observed.

Enantiomeric excesses can be enhanced above the values illustrated in Table I via the addition of chelating reagents and silating reagents to the reaction mixture. Such additions are known to improve optical purity in the stoichiometric reactions. As will be seen in the following sections, addition of chelating and silating reagents in the catalytic reactions has been shown to provide products having enantiomeric excesses of approximately 80%.

The invention will now be more particularly pointed out in the following examples.

EXPERIMENTAL SECTION

Methods and Materials. Tropocoronands were synthesized according to methods described by Zask et al., *Inorg. Chem.*, 25, 3400 (1986), and Imajo et al., *J. Am. Chem. Soc.*, 105, 2071 (1983). The 2-(tosyloxy)tropone was prepared by the method described by Doering et al., *J. Am. Chem. Soc.*, 74, 5688 (1952), from commercially available tropolone (Lancaster Synthesis or Aldrich Chemical Company). Lithium and Grignard reagents were purchased and used as received from Aldrich except for n-butyllithium (n-BuLi), which was titrated to determine the active alkyllithium content. Tetrahydrofuran (THF) was distilled from sodium benzophenone ketyl and flushed with argon for at least 15 min prior to use. Standard Schlenk techniques were used in handing all air-sensitive compounds and reaction mixtures.

Elemental analyses were performed by Schwarzkopf Microanalytical Laboratories (Woodside, N.Y.). Proton and carbon-13 NMR spectral analyses were carried out on a Bruker 250 or Varian XL-300 FT instrument, using deuteriochloroform or tetrahydrofuran-$d_8$ distilled from sodium benzophenone ketyl and stored in small ampules (1 mL). Chemical shifts are reported in ppm downfield from tetramethylsilane (TMS). Infrared spectra (KBr) were recorded on an IBM Instruments IR/30S FTIR spectrophotometer.

Gas chromatographic analyses were performed by using a Hewlett-Packard (HP) Model 5890 gas chromatograph, equipped with a flame-ionization detector (FID) and an HP-3393A integrator. An HP-1 methylsilicone gum 0.53×10 m fused silica column was used for separations. Conditions included a column head pressure of 10 psig and a temperature gradient program which held the initial oven temperature at 80° C. for 2 min, followed by gradual heating at a rate of 20°/min to a final oven temperature of 200° C. Products were identified by coinjection with authentic samples purchased commercially or prepared by unambiguous routes. Cyclohexenone, 12-crown-4, and (R)-α-methylbenzylamine were purchased from Aldrich and stored over 4 A molecular sieves. Tetrakis(acetonitrile)copper(I) tetrafluoroborate, [Cu(NCCH$_3$)$_4$](BF$_4$), was prepared and stored in a nitrogen-filled glovebox. CuBr.Me$_2$S was obtained from Aldrich and also stored in the drybox.

Preparative HPLC was carried out by using a Waters Associates PrepLC 500 instrument equipped with a refractive index detector and a PrepPAK/SILICA 500 cartridge.

Synthesis of 2-[(R)-α-Methylbenzylamino]Tropone

A flame-dried 500 mL three-necked round-bottomed flask equipped with a Teflon-coated magnetic stirrer bar, reflux condenser, and rubber septa was charged with 2-(tosyloxy)-tropone (15.6 g, 56.5 mmol), triethylamine (9.0 mL, about 65 mmol), (R)-α-methylbenzylamine (8.0 mL, about 62 mmol), and anhydrous ethanol (150 mL). The mixture was heated under reflux for 18 h. The resulting dark solution was allowed to cool to room temperature and concentrated under vacuum. The residual dark brown oil was dissolved in diethyl ether (300 mL) and washed consecutively with aqueous saturated ammonium chloride solution (1×100 mL) and aqueous sodium chloride solution (half saturated, 1×100 mL), and dried (MgSO$_4$). The solution was diluted to ⅓ of its original volume with pentane and filtered through a two-tiered column of activated alumina over silica gel (0.5 inch height×3.0 inch base diameter of each). Concentration of the yellow filtrate gave a yellow solid which was recrystallized from hot ether/pentane (about 2:1, v/v) to give bright yellow needles of compound 3 (7.4 g, 58% yield). Mp 84°–85°. $[\alpha]^{25}_D$ (CDCl$_3$)=−626.1°. Spectroscopic data: IR (KBr, cm$^{-1}$) 3289 (s, N—H), 2967 (w), 1604 (s), 1590 (s), 1544 (s), 1508 (s), 1475 (s), 1459 (s), 1448 (s), 1404 (s), 1389 (m), 1377 (m), 1361 (m), 1263 (m), 1208 (m), 1136 (m), 1087 (w), 1067 (w), 767 (w), 727 (s), 698 (s), 608 (w). $^1$H NMR (250 MHz, CDCl$_3$, 296° K.) δ 7.57 (1 H, br), 7.37-7.14 (7 H, complex m), 7.02 (1 H, t, J=10 Hz), 6.60 (1 H, complex m), 6.34 (1 H, d, J=10 Hz), 4.66 (1 H, quintet, J=6.8 Hz), and 1.64 (3 H, d, J=6.8 Hz). Anal. Calcd for C$_{15}$H$_{15}$NO: C, 79.97; H, 6.71; N, 6.22. Found: C, 79.53; H, 7.30; N, 5.83.

Preparation of 1-[(R)-α-Methylbenzylamino]-7-[(R)-α-Methylbenzylimino]-1,3,5-Cycloheptatriene 2-[(R)-α-methylbenzylamino] tropone (4.80 g, 21 mmol) dissolved in 50 mL of toluene was heated under reflux and treated with neat dimethylsulfate (2.2 mL, about 1.1 equiv), dropwise via syringe using extreme care. The mixture was heated and stirred under N$_2$ for 1.5 h, after which time a dark oil had separated.

The toluene was decanted, and the oil was allowed to cool to room temperature. Water (150 mL) was added, and the aqueous solution was transferred to a separatory funnel. The solution was made basic by the addition of aqueous 5% sodium carbonate (10 mL) and was extracted with methylene chloride (3×75 mL). The combined organic phases were dried (Na$_2$CO$_3$), filtered, and concentrated to give a dark oil (3.1 g, 60%). The oil was dissolved in anhydrous ethanol (150 mL) and treated with neat (R)-α-methylbenzylamine (1.75 mL, about 1.05 equiv). The dark solution was stirred at room temperature for 110 h. The reaction was concentrated in vacuo to yield a dark oil which was dissolved in ether (250 mL), washed with an aqueous saturated ammonium chloride solution (1×50 mL), diluted with hexane (80 mL), and dried ($Na_2CO_3$). The mixture was filtered through a two-tiered alumina/silica column. TLC analysis of the filtrate (ether:hexane eluent, 3:1 v/v) showed two spots corresponding to 1-[(R)-α-methylbenzylamino]-7-[(R)-α-methylbenzylamino]-1,3,5-cycloheptatriene, ($R_f$=0.7) and unreacted 2-[(R)-α-methylbenzylamino]tropone, ($R_f$=0.3). The product was purified by preparative liquid chromatography (PrepPAK/Silica 500; $Et_2O$: Hexane eluent, 3:1 v/v) to yield an oily product (2.75 g, 65%). The crude oil was dissolved in a minimum of methanol, and water was added to turbidity. The solution was allowed to stand overnight at room temperature with the formation of yellow-gold needles of compound 4. $M_p$, 74°. $[α]D^{22}(CDCl_3)=-919.7°$. The aminotroponeiminate portion of compound 4 will henceforth be abbreviated CHIRAMT. Spectroscopic data: IR (neat liquid, $cm^{-1}$) 3220 (br, N—H), 3085 (sh, w), 3065 (m), 3030 (m), 2975 (s), 2930 (m), 2870 (m), 1600 (s), 1545 (s), 1520 (s), 1480 (sh, s), 1477 (s), 1464 (s), 1430 (m), 1400 (s), 1390 (s), 1288 (s), 1230 (s), 1159 (m), 1103 (m), 1046 (m), 901 (m), 781 (sh, s), 770 (s), 720 (s), 576 (m). $^1H$ NMR (250 MHz, $CDCl_3$, 296° K.) δ7.41-7.28 (8 H, complex m), 7.27-7.19 (2 H, complex m), 6.61 (2 H, dd, J=9.7, 12.0 Hz), 6.23 (2 H, d, J=11.7 Hz), 6.06 (1 H, t, J=10.0 Hz), 4.76 (2 H, quartet, J=7.0 Hz), and 1.59 (6 H, d, J=7.0 Hz). Anal. Calcd. for $C_{23}H_{24}N_2$: C, 84.11; H, 7.37; N, 8.53. Found C, 83.94; H, 7.39; N, 8.50.

Preparation of 1-[(R)-1-(1'-Naphthyl)-Ethylamino]-7-[(R)-1-(1'-Naphthyl)Ethylimino]-1,3,5-Cycloheptatriene, H(NEAT)

H(NEAT) was prepared following the procedure for the preparation of H (CHIRAMT) described previously. Spectroscopic data are presented below.

[(R)-1-(1'-naphthyl)ethylamino]tropone: (mp. 150°-151° C.), ) $^1H$-NMR($CDCl_3$), 270 MHz:δ7.96 (1H, d, J=8.2 Hz), 7.78 (1H, d, J=7.7 Hz), 7.76-7.04 (8H, complex m), 6.77 (1H, t, J=10.2 Hz), 6.43 (1H, m), 6.03 (1H, d, J=10.4 Hz), 5.29 (1H, quintet, J=6.47 Hz), 3.30 (3H, d, J=6.72 Hz).

1-[(R)-1-(1'-naphthyl)ethylamino]-7-[(R)-1-(1'-naphthyl)ethylimino]-1,3,5-cycloheptatriene: $^1H$-NMR ($CDCl_3$), 250 MHz : δ8.28 (2H, d, J=8.3 Hz), 7.90 (2H, d, J=7.5 Hz ), 7.75 (2H, d, J=8.0 Hz), 7.59-7.39 (8H, complex m), 6.51 (2H, dd, J=9.76, J=11.0 Hz), 6.13 (2H, d, J=11.1 Hz), 6.00 (1H, t, J=9.2 Hz), 5.50 (2H, quartet, J=6.6 Hz ), 1.78 (6H, d, J=6.6 Hz).

Conjugate Addition Utilizing Chiral Catalysts. The following is a typical procedure for the synthesis of 3-substituted cyclohexanones using catalytic amounts of alkylcopper(I) complexes of the lithium salt Li[CuR(CHIRAMT)] (R=Ph, Bu, and Me).

A THF (5 mL) suspension of $CuBr.Me_2S$ (26.3 mg, 0.128 mmol) was treated with 1.0 equiv of n-BuLi at −78° C. under an argon atmosphere. The mixture was allowed to warm up slightly with the formation of a bright yellow solid. The mixture was again cooled to −78° C. and treated with Li(CHIRAMT) formed from compound 4 (85.8 mg, 0.261 mmol) and n-BuLi (1.0 equiv). The yellow slurry was stirred with gradual warming until a homogeneous burgundy solution was obtained. In the case of R—Me, a homogeneous mixture was not obtained even after prolonged stirring at room temperature, and it was evident that unreacted $(CuMe)_n$ was still present. The solution was cooled to −78° C. and THF (8 mL each) solutions of n-BuMgCl (25.0 equiv) and cyclohexenone (0.3068 g, 3.19 mmol) were added dropwise and simultaneously over a 5 min period. The resulting reaction mixture was stirred for an additional 10 min at −78° C., quenched with saturated aqueous $NH_4Cl$ solution (7 mL), and worked up as described in the previous section. Pure 3-butylcyclohexanone (0.4617 g, 94%) was obtained as checked by glc.

3-Phenylcyclohexanone (93% yield) was obtained by this method using a PhMgCl:Li[CuPh(CHIRMAT)] ratio of 25:1. The reaction involving the methyl derivative again proved to be sluggish, giving a product mixture (28% combined yield) comprised of about 20% 1,2-addition product and the remainder, 3-methylcyclohexanone. Note that due to the catalytic nature of the reaction, the alkyl groups of the Grignard and copper(I) species need not be the same.

Li[CuBr(CHIRAMT)] as Catalyst.

A THF (8 mL) suspension of $CuBr.Me_2S$ (13.1 mg, 0.064 mmol) was treated with THF (7 mL) solution of Li(CHIRAMT), prepared from 4 (21.0 mg, 0.064 mmol) an n-BuLi (1.0 equiv), at −78° C. under argon. The mixture was allowed to warm up with stirring until a homogeneous red-brown solution was obtained (about 20 min). The solution was cooled to −78° C., and THF (8 mL each) solutions of cyclohexenone (0.308 g, 3.20 mmol) and n-BuMgCl (3.20 mmol) were then added dropwise and simultaneously. The resulting yellow-green solution was stirred at −78° C. for an additional 5 min, quenched with a saturated aqueous ammonium chloride solution, and worked up in the usual manner. The product mixture (0.3585 g, 73%) contained some 1,2-addition product (<5%) along with the desired 3-butylcyclohexanone. Conversion to the ketal as previously described and analysis by $^{13}C$ NMR showed an enantiomeric excess of 14.5%.

Synthesis of [Li(12-crown-4)$_2$][$Cu_2$[$Cu_2$(μ-Br)(TC-5,5)

Neat 12-crown-4 (130 uL, about 0.80 mmol) was added to a THF (8 mL) suspension of $CuBr.Me_2S$ (92.4 mg, 0.45 mmol) under argon. The mixture was stirred, cooled to −78° C., and treated with a THF (8 mL) solution of $Li_2$(TC-5,5), prepared from $H_2$(TC-5,5) (68.6 mg, 0.18 mmol) and n-BuLi (2.0 equiv). The initial yellow-green reaction mixture turned amber over the course of the next 0.5 h at −78° C. The cooling bath was removed, and the mixture was allowed to warm up to 0° C. After 0.5 h, a red-brown precipitate had formed. The mixture was concentrated in vacuo and transferred to a drybox. The solid was collected by filtration and washed a few times with ether:THF (1:1, v/v), leaving an orange powder (190 mg, 111% yield) contaminated with [Li(12-crown-4)$_2$]Br, a cream colored solid. Recrystallization from THF proved to be difficult since the product is only sparingly soluble in this solvent. Mixtures of small red crystals and red amorphous powder were usually obtained from dilute THF solutions stored at −20° F. in the drybox. Combined yield, 72.0 mg (42%). Spectroscopic data: IR (KBr, $cm^{-1}$) 2910 (m), 2842 (m), 2809 (m), 1585 (s), 1500 (s), 1470 (s), 1453 (m), 1416 (s), 1386 (s), 1365 (m), 1347 (m), 1304 (w), 1289 (m), 1266 (m), 1227 (m), 1208 (w), 1134 (s), 1097 (s), 1024 (s), 992 (w), 925 (m), 885 (w), 856 (m), 768 (w), 724 (s). $^1H$ NMR (300 MHz, THF-d$_8$, 296° K.) δ6.60 (4 H, J=9.8, 11.4 Hz), 6.16 (4 H, d, J=11.4 Hz), 5.69 (2 H, t, J=9.8 Hz), 3.58 partially obscurred by solvent peaks (s, crown protons), 3.06 (4 H, t, J=13.0 Hz), 2.45 (4 H, quartet, J=13.0 Hz), 1.80 overlapping with solvent peaks (about 12 H, complex m). $^{13}$C NMR (75.5 MHz, THF-d$_8$, 295° K.) δ162.30, 132.80, 110.54, 108.76, 70.65, 51.84, 33.10, and 30.31. Anal. Calcd for C$_{40}$H$_{62}$BrN$_4$O$_8$Cu$_2$Li: C, 51.06; H, 6.64; Br, 8.49. Found: C, 50.86; H, 6.75; Br, 8.11.

Synthesis of [Li(12-crown-4)$_2$][Cu$_2$(μ-Ph)(TC-5,5)]

A THF (8 mL) suspension of [Cu(NCCH$_3$)$_4$](BF$_4$) (137.6 mg, 0.437 mmol) was cooled to −78° C. and treated with PhLi (0.384 mmol) under argon. The mixture was stirred for 10 min, treated with neat 12-crown-4 (270 μL, about 1.67 mmol), and allowed to warm up gradually to 0° C. The light red solution was stirred at 0° C. for 10 min and recooled to −78° C. whereupon a THF (8 mL) solution of Li$_2$(TC-5,5), prepared from H$_2$(TC-5,5) (72.1 mg, 0.191 mmol) and n-BuLi (0.384 mmol), was added dropwise via syringe. The burgundy mixture was allowed to warm up to room temperature with stirring (10 min), filtered, and concentrated in vacuo. The red solid was transferred to the drybox and washed with anhydrous ether (3×10 mL). The orange solid was very soluble in THF, and dark red irregularly shaped crystals were obtained from THF solutions scored at −20° F. (85.4 mg, 47.7%). Like the compound of the previous example, crystals of [Li(12-crown-4)$_2$][Cu$_2$(μ-Ph)(TC-5,5)] are air-sensitive and turn black within seconds of exposure. Sealed solutions of [Li(12-crown-4)$_2$]-[Cu$_2$(μ-Ph)(TC-5,5)] kept at room temperature also turn brown, eventually forming a dark precipitate. Spectroscopic data: IR (KBr, cm$^{-1}$) 3040 (w), 2918 (m), 2840 (m), 1586 (s), 1503 (s), 1471 (m), 1452 (s), 1417 (s), 384 (m), 1360 (m), 1302 (m), 1287 (m), 1264 (s), 1224 (m), 1135 (m), 1097 (s), 1024 (s), 926 (m), 885 (w), 855 (w), 717 (m). $^1$H NMR (300 MHz, THF-d$_8$, 295° K.) δ8.23 (2 H, complex m), 6.92-b 6.82 (3 H, complex m), 6.54 (4 H, dd, J=8.8, 11.6 Hz), 6.14 (4 H, d, J=11.6 Hz), 5.63 (2 H, t, J=8.8 Hz), 3.77 (4 H, complex m), 3.44 (crown protons, s), 2.87 (2 H, doublet of triplets, J=13.1, 8.2 Hz), 2.43 (4 H, complex m), 1.96-1.76 overlapping with solvent peaks (8 H, complex m), and 0.96 (2 H, complex m). $^{13}$C NMR (75.5 MHz, THF-d$_8$, 295° K.) δ162.07, 145.35, 132.33, 129.04, 126.24, 125.36, 110.67, 107.92, 70.39, 50.77, 31.74, and 26.89. Anal. Calcd for C$_{46}$H$_{67}$N$_4$O$_8$Cu$_2$Li: C, 58.90; H, 7.20; N, 5.97. Found: C, 58.81; H, 7.36; N, 6.05.

The Conjugate Addition of Grignard Reagents to Cyclohexenone Using Copper(I) Tropocoronand Catalysts Prepared In Situ A suspension of CuBr.Me$_2$S (38.3 mg., 0.186 mmol) in THF (5 mL) was treated at −78° C. with PhLi (1.0 equiv) under an atmosphere of argon. The mixture was allowed to stir above the cooling bath for a few minutes and then recooled to −78° C. A THF (7 mL) solution of Li$_2$(TC-5,5), prepared from H$_2$(TC-5,5) (35.0 mg, 0.093 mmol) and N-BuLi (2.0 equiv), was then added dropwise via syringe. The slurry was allowed to warm up until a clear homogeneous burgundy solution was obtained (2–3 min). The solution was then recooled to −78° C. Two THF (8 mL each) solutions, one containing 2-cyclohexen-1-one (0.444 g, 4.623 mmol) and the other containing phenylmagnesium chloride (4.62 mmol), were then added dropwise and simultaneously via syringe. After the additions were complete, the mixture was stirred at −78° C. for 10 min and quenched with a saturated aqueous ammonium chloride solution (7 mL). The mixture was diluted with ether (50 mL) and transferred to a 250 mL separatory funnel. The aqueous layer was extracted with fresh ether (2×20 mL), and the combined organic layers were washed with aqueous saturated sodium bicarbonate (25 mL), dried (MgSO$_4$), and concentrated in vacuo. The residue was mixed with ether:hexane (2:5, v/v) to precipitate a macrocycle (methanol may also be used for this purpose). Passage through a short silica gel column and removal of the solvents provided a dark liquid (0.684 g, 85% yield, based on cyclohexenone) which was 97% 3-phenylcyclohexanone by glc. Traces of biphenyl and the product from 1,2-addition were also detected.

By using the same method, a red-brown solution was obtained from the complexation of (CuBu)$_n$ and Li$_2$(TC-5,5). Treatment of the catalyst solution with cyclohexenone and n-BuMgCl (25 equiv each/Cu) at −78° C. and subsequent work-up as above provided 3-butylcyclohexanone (79% isolated yield), free of any 1,2-addition product.

The Michael-like addition of methylmagnesium chloride to cyclohexenone in the presence of catalytic amounts of "Li[Cu$_2$Me(TC-5,5)]" prepared as above from (CuMe)$_n$ and Li$_2$(TC-5 5) proceeds with a regioselectivity of only about 4:1 (1,4- vs 1,2-addition) although the stoichiometric reaction between the reagent formed by the addition of 2.0 equiv of MeLi to Li[Cu$_2$Me(TC-5,5)] and 2.0 equiv of cyclohexenone is regiospecific in favor of the Michael adduct. These results, obtained in the catalytic mode of reaction, may reflect unfavorable rates of formation and reactivity of the active molecular species when R is methyl.

[Li(12-Crown-4)$_2$][Cu$_2$(μ-Br)(TC-5,5)] as Catalyst

Solid [Li(12-crown-4)$_2$][Cu$_2$(μ-Br)(TC-5,5)] (20 mg, about 0.02 mmol) was placed in a flame-dried 50-mL round-bottomed flask equipped with a Teflon-coated magnetic stir bar. After the addition of THF (5 mL), the amber mixture was cooled to −78° C. and treated with 1.0 mL of a THF solution (9.0 mL total) of n-BuMgCl (3.2 mmol). After 10 min at −78° C., the mixture was treated with a THF (9.0 mL) solution of cyclohexenone (0.298 g, 3.1 mmol) added dropwise and concurrently with the remainder of the Grignard reagent. After an additional 10 min, the mixture was quenched with a saturated aqueous ammonium chloride solution (10 mL) and worked up as before (vide supra). The product mixture (0.2455 g, 51%) was analyzed by glc and was found to contain the 1,2-addition product (about 20%), as well as the desired 3-butylcyclohexanone (about 80%).

[Li(12-Crown-4)$_2$][Cu$_2$(μ-Ph)(TC-5,5)] as Catalyst

Red crystals of [Li(12-crown-4)$_2$]-[Cu$_2$(μ-Ph)(TC-5,5)] (4.0 mg, 4.3 μmol) were dissolved in THF (4 mL) under an argon atmosphere. The light red solution was cooled to −78° C. and treated with THF (250 μL each) solutions of cyclohexenone and n-BuMgCl (0.213 mmol each) added dropwise and simultaneously. The reaction mixture was stirred at −78° C. for an additional 5 min, quenched, and worked up in the manner described above to yield 0.0203 g (62%) of a mixture shown by glc analysis to be composed of the 1,4- and 1,2-addition (R—Bu) products in 6:1 ratio.

(Naphthylethylaminotroponeimine) Reagent Catalysts

A 5 ml suspension of CuBr.Me$_2$S in THF was treated with a slight excess of Li(NEAT) in 5 mL of THF. The Li(NEAT) was the reaction product of 1-[(R)-1-(1′-naphthyl)ethylamino]-7-[(R)-1-(1′-naphthyl)e- thylimino]-1,3,5-cycloheptatriene and n-BuLi (1 eq.) at −78° C. under an argon atmosphere.

The solution containing Li(NEAT) and CuBr.(Me)$_2$S was a yellow slurry which was stirred with gradual warming until a homogeneous burgundy solution was obtained. The solution was filtered through glass wool under an argon atmosphere and cooled to −78° C.

HMPA was added to the solution and the mixture was stirred until the HMPA had fully dissolved (about 5 min.). TMEDA can also be used with equal facility. Separate THF (5 mL) solutions of n-BuMgCl and a mixture of cyclohexenone and a silyl compound were added dropwise and simultaneously to the burgundy catalyst solution over 20–30 min. The resulting reaction mixture was stirred for an additional 5 min. at −78° C. and then quenched with 10 mL of water.

The mixture was diluted with ether (30 mL) and transferred to a 250 mL separatory funnel. The organic layer was washed with water four times (20 mL each), dried with K$_2$CO$_3$ and concentrated in vacuo. The residue was applied over an alumina column (2×20 cm). Elution with n-hexane/Et$_2$O (1:1) gave a yellow compound. Elution with Et$_2$O yielded pure 3-butylcyclohexanone. The results for nine representative examples are given in Table II below.

TABLE II

Enantioselectivity and Yields Using Chiral Catalysts in the Presence of Silane and HMPT Additives

| Entry[a] | Special Condition | Silane | mole fraction/enone | | | % | % ee |
|---|---|---|---|---|---|---|---|
| | | | Cu | Silane | HMPT | | |
| 1 | | Me$_3$SiCl | 0.05 | 1.8 | 1.8 | 95 | 51 |
| 2 | | Me$_3$SiCl | 0.09 | 1.7 | 1.7 | 98 | 60 |
| 3 | Toluene | Me$_3$SiCl | 0.04 | 2.0 | 0 | 63 | 0 |
| 4 | | $^t$Bu$_2$PhSiCl | 0.05 | 1.9 | 1.8 | 26 | 70 |
| 5 | | $^t$Bu$_2$PhSiCl | 0.04 | 1.9 | 1.9 | 53 | 74 |
| 6 | | $^t$Bu$_2$MeSiOTf | 0.03 | 1.8 | 1.3 | 39 | 79 |
| 7 | | $^t$Bu$_2$MeSiOTf | 0.03 | 1.8 | 0.3 | 24 | 15 |
| 8 | | $^i$Pr$_3$SiOTf | 0.04 | 2.0 | 1.3 | 98 | 44 |
| 9 | | $^t$Bu$_2$PhSiCl | 0.04 | 1.9 | 1.9 | 57 | 74 |
| 10 | LiN(SiMe$_3$)$_2$ | $^t$Bu$_2$PhSiCl | 0.03 | 2.0 | 2.0 | 57 | 73 |
| 11 | | $^t$Bu$_2$Si(OTf)$_2$ | 0.03 | 1.0 | 2.0 | 67 | 40 |
| 12 | R = Ph | Me$_3$SiCl | 0.04 | 2.0 | 2.0 | 96 | 0 |
| 13 | cyclopentenone | $^t$Bu$_2$PhSiCl | 0.04 | 2.0 | 2.0 | 46 | 0 |
| 14 | NaH | $^t$Bu$_2$PhSiCl | 0.03 | 1.9 | 2.0 | 39 | 61 |

[a]Entries 1–8 use Li[CuBr(NEAT)]. Entries 9–13 use Li[CuBr(CHIRAMT)] and Entry 14 used Na[CuBr(CHIRAMT)].

The yields reported in runs 1 and 3–8 of Table II are the isolated yields; the low values in runs 4–7 are due to incomplete separations. In runs 2 and 8, the yields are GC yields are calculated based on the amount of unreacted reactant. In runs 1–3 and 12, the silyl compound is Me$_3$SiCl; in runs 4, 5, 9, 10 and 13–14, the silyl compound is phenyl$_2$(t-Bu)SiCl; in runs 6–7, the silyl compound is (t-Bu)$_2$MeSiOTf; and in run 8, the silyl compound is (i-Pr)$_3$SiOTf. In these runs, the term Tf in reference to the silyl compound refers to trifluoromethanesulfonate. In run 3, the solvent is toluene. In runs 9 and 14, the catalytic ligand is H(R-CHIRAMT).

Conversion to the Diastereometric Ketals and Analysis By $^{13}$C NMR

A toluene (5 mL) solution of the 3-substituted cyclohexanone (2.0 mmol), (R,R)-2,3-butanediol (3.4 mmol), tosic acid (0.1 mmol), and solid magnesium sulfate (about 10 mg) was heated under reflux (3–5 h). The mixture was cooled and concentrated under vacuum. The residue was dissolved in ether and chromatographed through a disposable pipette containing activated alumina (about 3 cm). The filtrate was concentrated in vacuo, and the liquid (usually greater than 90% isolated yield) dissolved in deuteriochloroform. A $^{13}$C NMR spectrum was recorded, and a comparison of the integrated carbon resonances provided an estimate for the relative amounts of diastereomers present.

Equivalents

Those skilled in the art will know, or be able to ascertain using no more than routine experimentation, many equivalents to the specific embodiments expressly described herein. These are intended to be within the scope of the invention as described by the claims herein.

We claim:

1. An optically active complex of the formula:

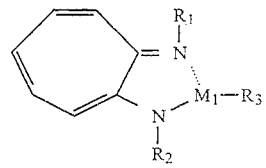

wherein R$_1$ and R$_2$ are chiral hydrocarbon groups with or without heteroatom substituents having 4 to 24 carbon atoms, wherein R$_1$ and R$_2$ are the same or different, and wherein R$_3$ is a negatively charged group or a hydrocarbon group having 1 to 24 carbon atoms and M$_1$ is a transition metal.

2. The complex of claim 1 wherein the chiral hydrocarbon groups are selected from the group consisting of aliphatic groups, aromatic groups and combinations thereof.

3. The complex of claim 2 wherein the chiral hydrocarbon groups contain heteroatom substituents.

4. The complex of claim 1 wherein R$_1$ and R$_2$ are the same.

5. The complex of claim 1 wherein R$_1$ and R$_2$ each independently represent chiral hydrocarbon groups selected from the group consisting of (R)-1-phenylethyl, (S)-1-phenylethyl, (R)-1-(1'-naphthyl)ethyl, (S)-1-(1'-naphthyl)-ethyl, (R)-1-(9'-anthracenyl) ethyl, (S)-1-(9'-anthracenyl) ethyl, D-(−)-alanine, L-(+)-alanine, (R)-2-amino-3-phenyl-1-propanol, (S)-2-amino-3-phenyl-1-propanol, (R)-(−)-1-amino-2-propanol, S-(+)-1-amino-2-propanol, (R)-2-amino-1-propanol, (S)-2-amino-1-propanol, (R)-amphetamine, L-amphetamine, (R)-norbornylamine, (S)-norbornylamtne, (R)-fenchylamine, (S)-fenchylamine, (R)-bornylamine, (S)-bornylamine, 1-(R)-2-(S)-norephedrine and 1-(S)-2-(R)-norephedrine.

* * * * *